United States Patent
Bischoff et al.

(10) Patent No.: US 9,474,647 B2
(45) Date of Patent: Oct. 25, 2016

(54) EYE SURGERY REFRACTION CORRECTION

(71) Applicant: Carl Zeiss Meditec AG, Jena (DE)

(72) Inventors: Mark Bischoff, Jena (DE); Gregor Stobrawa, Jena (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 14/025,868

(22) Filed: Sep. 13, 2013

(65) Prior Publication Data

US 2014/0288540 A1 Sep. 25, 2014

Related U.S. Application Data

(60) Provisional application No. 61/701,373, filed on Sep. 14, 2012.

(30) Foreign Application Priority Data

Sep. 14, 2012 (DE) .................. 10 2012 018 421

(51) Int. Cl.
*A61F 9/008* (2006.01)
*A61F 9/013* (2006.01)

(52) U.S. Cl.
CPC .............. *A61F 9/008* (2013.01); *A61B 34/10* (2016.02); *A61F 9/013* (2013.01); *A61F 2009/00872* (2013.01); *A61F 2009/00878* (2013.01)

(58) Field of Classification Search
CPC ..................... A61F 2009/00872; A61F 9/008
USPC ....................................... 606/4, 5
See application file for complete search history.

(56) References Cited

U.S. PATENT DOCUMENTS

| 5,656,186 | A | 8/1997 | Mourou et al. |
|---|---|---|---|
| 6,325,509 | B1 * | 12/2001 | Hodur et al. ............ 351/159.14 |
| 6,325,792 | B1 * | 12/2001 | Swinger .............. A61F 9/00804 606/11 |
| 2004/0059320 | A1 | 3/2004 | Telandro et al. |
| 2008/0183159 | A1 | 7/2008 | Preuss et al. |
| 2008/0275433 | A1 | 11/2008 | Russmann et al. |
| 2009/0268155 | A1 * | 10/2009 | Weeber ................ A61F 2/1618 351/159.05 |
| 2009/0326650 | A1 * | 12/2009 | Zickler et al. ............... 623/5.11 |
| 2010/0331830 | A1 | 12/2010 | Bischoff et al. |
| 2010/0331831 | A1 | 12/2010 | Bischoff et al. |

FOREIGN PATENT DOCUMENTS

| DE | 69500997 | T2 | 4/1998 |
|---|---|---|---|
| DE | 102005040338 | A1 | 3/2007 |
| DE | 102006053120 | A1 | 5/2008 |
| DE | 102007019813 | A1 | 10/2008 |
| DE | 102007053283 | A1 | 5/2009 |
| DE | 102207053281 | A1 | 5/2009 |
| DE | 102008049401 | A1 | 4/2010 |

\* cited by examiner

*Primary Examiner* — William Thomson
*Assistant Examiner* — Jeffrey Lipitz
(74) *Attorney, Agent, or Firm* — Leydig, Voit & Mayer, Ltd.

(57) ABSTRACT

A planning device produces control data for a treatment device for eye surgery which produces at least one cutting surface in a cornea of the eye using a laser device. The planning device includes a calculation module for establishing a cornea cutting surface. The calculation module is configured to establish the cornea cutting surface based on data of a refraction correction, to produce a control data set for actuating the laser device for the cornea cutting surface, and to determine the cornea cutting surface in such a way that it consists of a plurality of sub-surfaces, each of which make a contribution to the refraction correction.

9 Claims, 3 Drawing Sheets

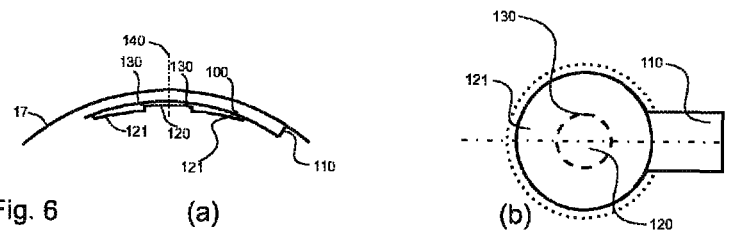
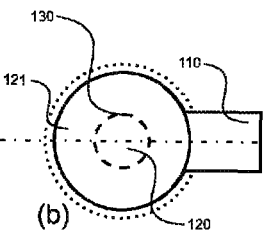
Fig. 6 (a) (b)
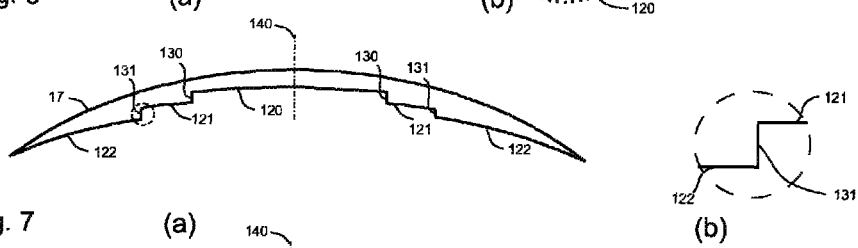
Fig. 7 (a) (b)
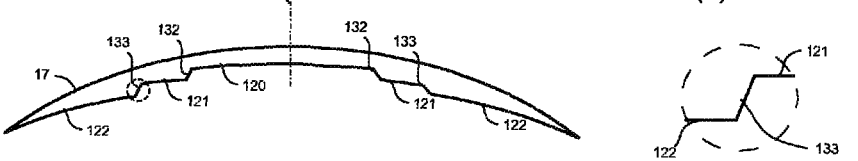
Fig. 8 (a) (b)
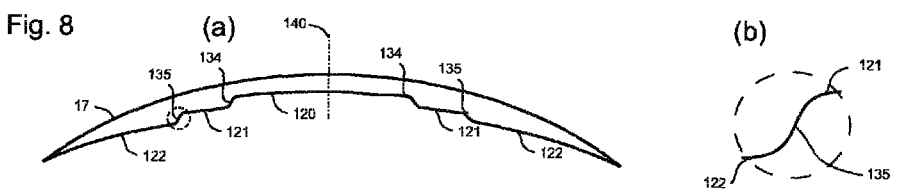
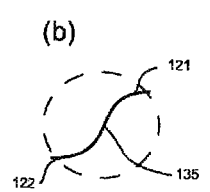
Fig. 9 (a) (b)
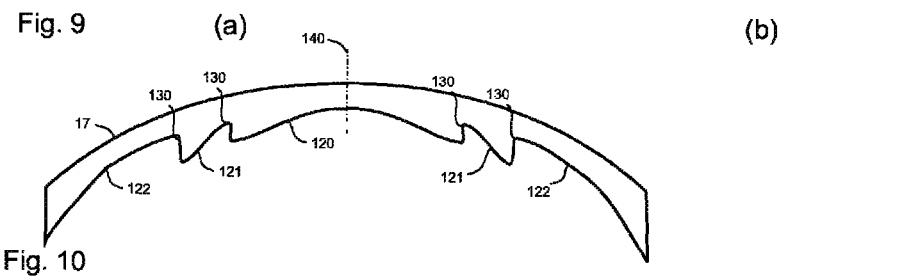
Fig. 10

EYE SURGERY REFRACTION CORRECTION

CROSS REFERENCE TO RELATED APPLICATIONS

This application claims priority from U.S. Provisional Patent Application No. 61/701,373, filed Sep. 14, 2012, and to the German Application No. 10 2012 018 421.2, filed Sep. 14, 2012, both of which is hereby incorporated by reference herein in its entirety.

FIELD

The invention relates to a planning device for producing control data for a treatment device which produces at least one cutting surface in the cornea by means of a laser device. The invention further relates to a treatment device which comprises a planning device of the stated type.

The invention further relates to a method for producing control data for a treatment device which produces at least one cutting surface in the cornea by means of a laser device.

Finally, the invention also relates to a method for eye surgery, at least one cutting surface being produced in the cornea by means of a treatment device comprising a laser device.

BACKGROUND

In the prior art, a wide range of treatment methods having the purpose of refraction correction in the human eye are known. In this context, the purpose of the operation methods is to alter the cornea selectively so as to influence the light refraction in the eye. A plurality of operation methods are used for this purpose. At present, what is known as laser-assisted in situ keratomileusis, also known as LASIK for short, is the most widespread. In this context, a cornea lamella is initially detached from the cornea surface on one side and folded to the side. This lamella can be detached by means of a mechanical microkeratome, or also by means of what is known as a laser keratome, such as is marketed for example by Intralase Corp., Irvine, USA. After the lamella has been detached and folded to the side, the LASIK operation provides the use of an excimer laser, which removes, by ablation, the corneal tissue which is exposed under the lamella in this manner. After the volume present under the cornea surface has been vaporised in this manner, the cornea lamella is folded back onto the original spot again.

The use of a laser keratome to expose the lamella is advantageous by comparison with a mechanical blade, since the geometric precision is improved and the frequency of clinically significant complications is reduced. In particular, the lamella can be produced with a much more constant thickness if laser radiation is used. The cut edge is also precisely formed, and this reduces the risk of healing difficulties as a result of this boundary surface which remains even after the operation. However, a drawback of this method is that two different treatment devices have to be used, specifically on the one hand the laser keratome for exposing the lamella and on the other hand the laser which vaporises the corneal tissue.

These drawbacks are eliminated in a method which was implemented very recently by Carl Zeiss Meditec. In this lenticule extraction method, a cutting geometry which separates a cornea volume (known as a lenticule) in the cornea is formed in the cornea of the eye by means of a short-pulse laser, preferably a femtosecond laser. This is then removed manually by the operator. One advantage of this method is that the cutting quality is further improved by the use of the femtosecond laser.

Moreover, only one treatment device is now necessary; the excimer laser is no longer used.

A development of the method is referred to in the literature as the SMILE method, in which instead of producing a flap, merely a small opening cut provides access to the lenticule positioned under what is known as the cap. The separated lenticule is removed through this small opening cut, damaging the biomechanical integrity of the anterior cornea less than in LASIK, FLEX or PRK. In addition, fewer nerve fibres in the cornea are cut up in this manner, and this has a demonstrably favourable effect on the restoration of the original sensitivity of the cornea surface. The symptom of dry eyes, which often has to be treated after LASIK, is thus reduced in intensity and duration. Other complications following LASIK, which generally relate to the flap (for example folding, epithelial ingrowth in the flap bed), occur more rarely with no flap.

When producing cutting surfaces in the cornea by means of laser radiation, the optical radiation effect is usually exploited in that an optical aperture is produced by means of individual optical pulses, the duration of which may be between 100 fs and 100 ns. It is also known to introduce individual pulses, the energy of which is below a threshold for an optical aperture, into the tissue or material with an overlap, in such a way that material or tissue separation is achieved in this way too. This idea for producing a cut in the corneal tissue makes a large number of cuts possible.

However, it is common to the different lenticule geometries that a lenticule is produced which—embedded in the treated cornea—corresponds to a conventional concave-convex lens, this lens being able to have much higher orders of correction (cylindrical, spherical aberration etc.). The correction effect in the vision correction carried out by means of lenticule extraction is based on the defined alteration of the radius of curvature of the cornea by removing the lenticule volume. A corresponding lenticule geometry is known to the person skilled in the art from DE102006053120 A1.

For the known method, it is basically irrelevant at what depth the lenticule is removed, so long as a sufficient and predictable effect on the anterior side of the cornea is achieved. It is also irrelevant exactly how the cut shape of the individual cuts is configured, just so long as the thickness of the tissue present between the two cuts follows the known relationships. However, it is thus immediately obvious that a minimum thickness is required for a particular refractive effect which is to extend over an optical zone having a particular extent. This is also known to the person skilled in the art from DE102006053120 A1. The lenticule must not be less than this minimum thickness. In the case of excimer laser correction too, in which tissue is vaporised, there is a corresponding lower thickness of the tissue to be vaporised.

This minimum thickness m of a lenticule is approximated by the following equations.

$$m = R_{CV} - R_{CV}^* - \sqrt{R_{CV}^2 - r^2} + \sqrt{R_{CV}^{*2} - r^2}$$

$$R_{CV}^* = \dfrac{1}{\dfrac{1}{R_{CV}} + \dfrac{B_{BR}}{(n_C - 1)(1 - d_{HS}) \cdot B_{BR}}} + F$$

$$F = \left(1 - \dfrac{1}{n_C}\right)(d_C^* - d_C)$$

In this context, $R_{CV}$ is the radius of curvature of the anterior side of the cornea, r is the diameter of the optical zone of the lenticule, $n_c$ is the refraction power of the cornea, $d_{HS}$ is the vertex distance of the cornea, $B_{BR}$ is the desired correction value (in dpt) and $d_C$ is the thickness of the cornea. In this context, the variables F, $R_{CV}$ and $d_C$ correspond to the respective state before the correction; the variables corresponding to the state after the correction are marked *. Like the other described relationships, the expression for F is a mathematically precise solution, which may not always be adhered to in reality. The resulting error correction would then have to be compensated in other ways, for example a transformation table for input parameters (nomogram). Finally, the relationship shown here would be obtained again in an approximation suitable for practical use.

For many refractive laser corrections this is unproblematic, but for large correction amounts it is sometimes not possible to carry out the refraction correction in such a way that the entire optical zone of the cornea of the treated eye undergoes the desired correction. The reason for this is the risk involved to the mechanical stability of the treated cornea, which could be deformed in an uncontrolled manner over a long period as a result. As a provisional solution, the correction is sometimes only carried out completely in a central region of the optical zone, and in the surrounding edge zone either no correction or a smaller correction is carried out. In these cases, a higher residual stromal tissue thickness (residual stromal thickness) is obtained, impairing the quality of the optical correction. This quality defect cannot be eliminated using the currently known methods.

SUMMARY

In an embodiment, the present invention provides a planning device that produces control data for a treatment device for eye surgery which produces at least one cutting surface in a cornea of the eye using a laser device. The planning device includes a calculation module for establishing a cornea cutting surface. The calculation module is configured to establish the cornea cutting surface based on data of a refraction correction, to produce a control data set for actuating the laser device for the cornea cutting surface, and to determine the cornea cutting surface in such a way that it consists of a plurality of sub-surfaces, each of which make a contribution to the refraction correction.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 6 is a schematic drawing of a first lenticule geometry according to the invention, FIG. 7 is a schematic drawing of a second lenticule geometry according to the invention, FIG. 8 is a schematic drawing of a third lenticule geometry according to the invention, FIG. 9 is a schematic drawing of a fourth lenticule geometry according to the invention, FIG. 10 is a schematic drawing of a fifth lenticule geometry according to the invention,

DETAILED DESCRIPTION

Figure 1:
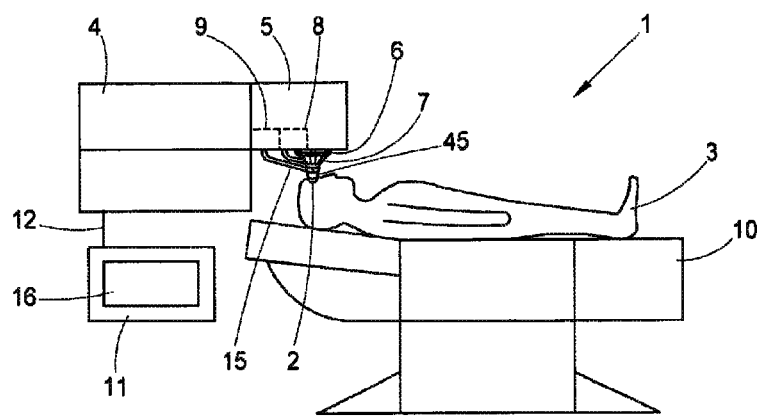
FIG. 1 is a schematic drawing of a treatment device comprising a planning device for a secondary treatment in eye surgery refraction correction.

An aspect of the present invention is to provide a planning device for producing control data, a treatment device for refraction correction eye surgery, and a method for producing control data for a treatment device of this type, in which stability of the cornea is ensured even in the case of very strong optical corrections.

In an embodiment, the present invention provides a planning device of the type mentioned at the outset which comprises a calculation module for establishing a cornea cutting surface, the calculation module determining the new cornea cutting surface in such a way that it consists of a plurality of sub-surfaces, which each individually make a contribution to the refraction correction.

In an embodiment, the present invention also provides a treatment device which comprises a laser device, which separates at least one cutting surface in the cornea by means of laser radiation in accordance with control data, and comprises a planning device of the type mentioned above for producing the control data, the planning device determining the new cornea cutting surface in such a way that it consists of a plurality of sub-surfaces, which each individually make a contribution to the refraction correction.

In an embodiment, the present invention also provides a method for producing control data in accordance with the type stated at the outset, comprising: producing a control data set for the cornea cutting surface for actuating the laser device, the planning device determining the new cornea cutting surface in such a way that it consists of a plurality of sub-surfaces, which each individually make a contribution to the refraction correction.

Finally, in an embodiment, the present invention provides a method comprising: producing a control data set for the cornea cutting surface, transferring the control data to the treatment device, and producing the cutting surfaces by actuating the laser device using the control data set, the new cornea cutting surface being determined when producing the control data set in such a way that it consists of a plurality of sub-surfaces, which each individually make a contribution to the refraction correction.

Thus, embodiments of the invention involve producing a radially stepped lenticule profile, similar to the Fresnel lens known to the person skilled in the art in the field of optics. In the field of refractive laser correction, this approach is initially of dubious effectiveness, since the resulting shape of the cornea surface is problematic in medical terms. The cornea surface, which substantially follows the shape of the removed lenticule, would result in a type of Fresnel lens in this case too. Again, however, this is not true in practical clinical terms, since the upper tissue layers (flap or cap) bring about immediate partial smoothing, and the epithelialisation which follows the operation in the healing phase also has a smoothing effect, and this changes the resulting visual impression. However, these effects can be clinically acceptable, and lead to appropriate aspect ratios for the patient, if the specific parameters of the stepping according to the invention are suitably selected.

In this context, stepping according to the invention involves implementing a more or less abrupt change in the lenticule thickness at a particular radius (or also ovally), but obtaining the curvature path as usual outside the area of the step. In this context, a step according to the invention is configured in such a way that the maximum lenticule thickness is reduced.

In a way, the invention also involves not providing the desired alteration to the radius of curvature continuously, but instead causing annular or oval zones inside the correction area to deviate therefrom. This compromise is ultimately the price for the possibility of going below the previously applicable minimum thickness of a lenticule.

In a first embodiment of the invention, the stepping is provided in such a way that the steps are orientated as exactly parallel to the optical axis as possible. For this purpose, the steps should be no higher than 100 µm, preferably no higher than 50 µm and usually no higher than 25 µm. Thus, even a single step of this type saves up to 25 µm (50 µm, 100 µm) of residual stromal thickness. A plurality of steps of this type may also be arranged concentrically, making it possible to save this amount several times over. This is preferable if the step size would otherwise exceed 25 µm or at most 50 µm.

For example, three steps of this type could be produced, a first at 3 mm, a second at 4 mm and a third at 5 mm diameter. If each of the steps is for example 20 µm high, this saves 60 µm of residual stromal thickness. This corresponds to a correction of approximately 4 dpt. If for example a stromal thickness reduction of approximately 155 µm would normally take placing during treatment for a correction of 12 dpt (13 µm per dpt as a rough guide), this amount could thus be reduced to less than 100 µm. With the same residual stromal thickness, an eye having a cornea only 450 µm thick could thus (assuming a flap or cap of 100 µm) be corrected by 12 dpt, instead of only 8 dpt. In general, a residual stromal thickness of 250 µm is found to be safe for LASIK (with a flap); this value is also considered safe for SMILE, although a smaller residual thickness appears to be clinically acceptable because of the higher biomechanical stability of the cap by comparison with the flap. Specifically, eyes with very large sight defects, for which complete correction was not previously possible, can thus be corrected even better with the novel method.

In some cases, it is usual not to extend very strong sight corrections (over 10 dpt) over the entire optical zone, since in this case the associated tissue removal would pose a risk to the biomechanical stability. The method according to the invention now makes it possible to extend even these strong corrections over the entire optical zone, a step expediently being placed in the lenticule approximately where the lenticule would have simply ended in the previous method.

In a second embodiment of the invention, the stepping is carried out in such a way that the steps are not orientated exactly parallel to the optical axis, but inclined or rounded, so as to promote the smoothing which takes place in any case through the tissue (flap cap) positioned above. In this case, the advantage of a geometry of this type is that no cavities (which fill with fluid) can be left in the interior of the stroma, and the epithelialisation reaches a stable state more rapidly and thus less regression occurs.

As well as for correcting myopia (with and without astigmatism), the method according to the invention is of particular benefit for correcting hyperopia.

With all of the previous methods, when correcting hyperopia, a satisfactory result is only obtained for small corrections (up to 3 dpt) in terms of rapid healing progression and long-term success of the LASIK treatment. In this context, the method according to the invention now makes it possible to reduce the large (deep) tissue removal, at the edge of the optical zone, which causes this problem.

It shall be understood that the features mentioned above and described in the following can be used not only in the specified combinations, but also in other combinations or in isolation, without departing from the scope of the present invention.

A treatment device for eye surgery is shown in FIG. 1 and provided with the general reference numeral 1. The treatment device 1 is formed for introducing laser cuts onto an eye 2 of a patient 3. For this purpose, the treatment device 1 comprises a laser device 4, which emits, from a laser source 5, a laser beam 6 which is directed into the eye 2 or the cornea of the eye as a focussed beam 7. Preferably, the laser beam 6 is a pulsed laser beam having a wavelength of between 300 nanometers and 10 micrometers. Further, the pulse length of the laser beam 6 is in the range of between 1 femtosecond and 100 nanoseconds, pulse repeat rates of 50 to 5000 kilohertz and pulse energies of between 0.01 microjoules and 0.01 millijoules being possible. The treatment device 1 thus produces a cutting surface in the cornea of the eye 2 by deflecting the pulsed laser radiation. A scanner 8 and a radiation intensity modulator 9 are therefore further provided in the laser device 4 or the laser source 5 thereof for this purpose.

The patient 3 is positioned on a bed 10 which is adjustable in three spatial directions so as to orientate the eye 2 appropriately with respect to the incidence of the laser beam 6. In a preferred construction, the adjustment of the bed 10 can be motor-driven.

The actuation may take place in particular via a control apparatus 11, which basically controls the operation of the treatment device 1 and is connected to the treatment device via suitable data connections, for example connection lines 12, for this purpose. Naturally, this communication may also take place in other ways, for example by fibre optics or wirelessly. The control apparatus 11 carries out the corresponding settings and time control in the treatment device 1, in particular the laser device 4, and thus implements corresponding functions of the treatment device 1.

The treatment device 1 also further comprises a fixing means 15, which fixes the cornea of the eye 2 in position with respect to the laser device 4. In this context, this fixing means 15 may comprise a known contact glass 45, against which the cornea is applied by negative pressure and which gives the cornea of the eye a desired geometric shape. Contact glasses of this type are known to the person skilled in the art from the prior art, for example from DE 102005040338 A1. The entire disclosure of this document, where it relates to the description of a construction of the contact glass 45 which is possible for the treatment device 1, is incorporated into the present document.

The treatment means 1 further comprises a camera which can take a picture of the cornea 17 of the eye through the contact glass 45. In this context, the illumination for the camera may be provided in both the visible and the infra-red range.

The control apparatus 11 of the treatment device 1 also further comprises a planning device 16, which will be explained in greater detail in the following.

Figure 2:
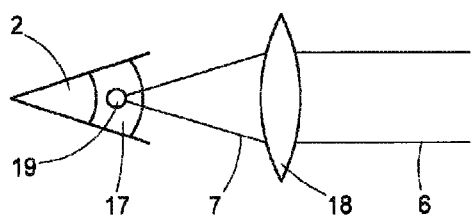
FIG. 2 is a schematic drawing of the effect of the laser radiation which is used in the treatment device of FIG. 1.

FIG. 2 shows schematically the operation of the incident laser beam 6. The laser beam 6 is focussed and is incident on the cornea 17 of the eye 2 as the focussed laser beam 7. Schematically illustrated optics 18 are provided for the focussing. In the cornea 17, they bring about a focus at which the laser radiation energy density is so high that, in combination with the pulse length of the pulsed laser radiation 6, a non-linear effect occurs in the cornea 17. For example, each pulse of the pulsed laser radiation 6 can produce at the focus 19 an optical aperture in the cornea 17 of the eye, which in turn initiates a plasma bubble (only shown schematically in FIG. 2). When the plasma bubble occurs, the tissue layer separation encloses an area greater than the focus 19, although the conditions for producing the optical aperture are only met at the focus 19. For an optical aperture to be produced by each laser pulse, the energy density, that is to say the fluence of the laser radiation, has to be above a particular threshold which is dependent on the pulse length. This relationship is known to the person skilled in the art for example from DE 69500997 T2. Alternatively, a tissue separation effect can also be achieved by way of pulsed laser radiation, in that a plurality of laser radiation pulses are emitted in a region where the focus spots overlap. A plurality of laser radiation pulses thus cooperate so as to achieve a tissue separation effect. However, the type of tissue separation used by the treatment device 1 is otherwise irrelevant to the following description; all that matters is that a cutting surface is produced in the cornea 17 of the eye 2.

So as to carry out an eye surgery refraction correction, a cornea volume is removed from the area inside the cornea 17 by means of the laser radiation 6, in that tissue layers are separated therein, which isolate the cornea volume and subsequently make it possible to remove it. For isolating the cornea volume which is to be removed, in the case of the laser radiation which is used in a pulsed manner, for example, the position of the focus 17 of the focussed laser beam 7 in the cornea 17 is adjusted. This is shown schematically in FIG. 3. The refraction properties of the cornea 17 are selectively altered by removing the volume, so as to bring about the refraction correction. The volume is therefore generally lens-shaped, and is referred to as a lenticule.

Figure 3:
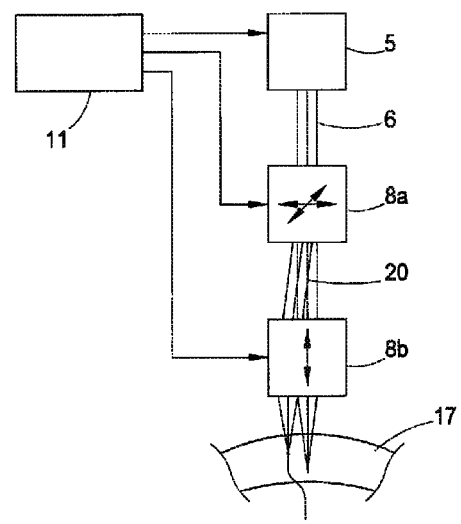
FIG. 3 is a further schematic drawing of the treatment apparatus of FIG. 1 relating to the introduction of the laser radiation.

In FIG. 3, the elements of the treatment device 1 are only included when they are necessary for understanding the cutting surface production. As stated above, the laser beam 6 is bundled at a focus 19 in the cornea 19, and the position of the focus 19 in the cornea is adjusted in such a way that energy focussed at different points from laser radiation pulses is introduced into the tissue of the cornea 17 to produce the cutting surfaces. The laser radiation 6 is preferably provided by the laser source 5 as pulsed radiation. In the construction of FIG. 3, the scanner 8 is constructed in two parts, and consists of an xy scanner 8a, which in a variant is formed by two substantially orthogonally deflecting galvanometer mirrors. The scanner 8a deflects the laser beam 6 from the laser source 5 in two dimensions, in such a way that after the scanner 9 there is a deflected laser beam 20. The scanner 8a thus brings about an adjustment in the position of the focus 19 substantially perpendicular to the primary direction of incidence of the laser beam 6 in the cornea 17. To adjust the depth, a z scanner 8b is provided as well as the xy scanner 8a in the scanner 8, and is for example in the form of an adjustable telescope. The z scanner 8b ensures that the z position of the position of the focus 19, that is to say the position thereof on the optical axis of incidence, is altered. The z scanner 8b can be arranged upstream or downstream from the xy scanner 8a.

For the operating principle of the treatment device 1, it is irrelevant how the individual coordinates are allocated to the spatial directions, and also whether the scanner 8a deflects about mutually perpendicular axes. Rather, any scanner may be used which can adjust the focus 19 in a surface not containing the axis of incidence of the optical radiation. Further, any non-Cartesian coordinate system may also be used for deflecting or controlling the position of the focus 19. Examples of this are spherical coordinates and cylindrical coordinates. The position of the focus 19 is controlled by means of the scanners 8a, 8b, actuated by the control apparatus 11, which applies corresponding settings to the laser source 5, the modulator 9 (not shown in FIG. 3) and the scanner 8. The control apparatus 11 ensures the suitable operation of the laser source 5 and the three-dimensional focus adjustment shown here by way of example in such a way that ultimately a cutting surface is formed which isolates a particular cornea volume which is to be removed for the refraction correction.

The controller 11 operates in accordance with predetermined control data which, in the laser device 4 shown here merely by way of example, are predetermined as target points for the focus adjustment. The control data are generally combined into a control data set. This results in geometric specifications for the cutting surface to be formed, for example the coordinates of the target points, as a pattern. In this embodiment, the control data set thus also includes specific place values for the focus position adjustment mechanism, for example for the scanner 8.

Figure 4:
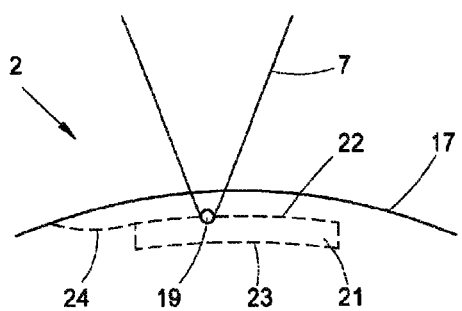
FIG. 4 is a schematic sectional view through the cornea of the eye to illustrate the removal of the volume of the cornea in connection with the eye surgery refraction correction.

The production of the cutting surface using the treatment device 1 is shown by way of example in FIG. 4. A cornea volume 21 in the cornea 17 is isolated by adjusting the focus 19 at which the focussed beam 7 is bundled. For this purpose, cutting surfaces are formed, shown here by way of example as an anterior flap cutting surface 22 and a posterior lenticule cutting surface 23. In this context, these terms should be understood to be merely exemplary, and are intended to provide a reference to the conventional LASIK or FLEX method for which the treatment device 1, as described above, is also configured. All that matters here is that the cutting surfaces 22 and 23 and edge cuts (not described further here), which bring the cutting surfaces 22 and 23 together at the edges thereof, isolate the cornea volume 21. Further, a cornea lamella which anteriorly defines the cornea volume 21 can be folded away by way of an opening cut 24, in such a way that the cornea volume 21 can be removed.

Alternatively, the SMILE method may be used, in which the cornea volume 21 is removed by way of a small opening cut, as disclosed in DE 10 2007 019813. The entire disclosure of this document is incorporated into the present document.

Figure 5:
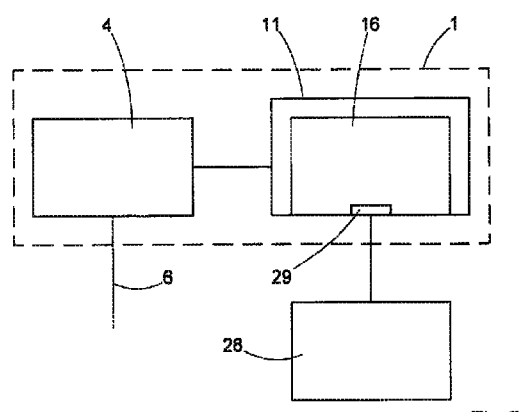
FIG. 5 is a schematic drawing relating to the construction of the treatment apparatus of FIG. 1, with particular emphasis on the planning device provided therein.

FIG. 5 shows schematically the treatment device 1, and by way of this the significance of the planning device 16 is to be described in greater detail. In this variant, the treatment device 1 comprises at least two modules. The previously described laser device 4 emits the laser beam 6 onto the eye 2. In this context, the laser device 4 is operated, as already shown, fully automatically by the control apparatus 11, that is to say upon a corresponding start signal the laser device 4 starts to produce and deflect the laser beam 6 and thus produces cutting surfaces which are constructed in the manner described above. The control signals required for the operation are received by the laser device 5 of the control apparatus 11, to which corresponding control data have previously been provided. This takes place by means of the planning device 16, which is shown in FIG. 5 merely by way of example as a component of the control apparatus 11. Naturally, the planning device 16 may also be formed independently and communicate with the controller 11 in a wired or wireless manner. All that matters in this case is that a corresponding data transfer channel is provided between the planning device 16 and the control apparatus 11.

The planning device 16 produces a control data set, which is provided to the control apparatus 11 for carrying out the eye surgery refraction correction. In this context, the planning device uses measurement data relating to the cornea of the eye. In the embodiment being described, these data originate from a measuring device 28, which has measured the eye 2 of the patient 2 previously. Naturally, the measurement device 28 may be configured, and convey the relevant data to the interface 29 of the planning device 16, in any desired manner.

The planning device now assists the operator of the treatment device 1 in establishing the cutting surface for isolating the cornea volume 21. This may go as far as fully automatically establishing the cutting surfaces, and this may take place for example in that the planning device 16 determines from the measurement data the cornea volume 21 to be removed, the delimiting surfaces of which are defined as cutting surfaces, and produces corresponding control data for the control apparatus 11 therefrom. At the other end of the automation scale, the planning device 16 may provide input options where a user inputs the cutting surfaces in the form of geometric parameters etc. Intermediate stages provide suggestions for the cutting surfaces, which are generated automatically by the planning device 16 and can subsequently be modified by a user. In principle, all of the ideas explained previously in the more general part of the description above may be applied in the planning device 16 in this context.

So as to carry out treatment, the planning device 16 produces control data for the cutting surface production, which are subsequently used in the treatment device 1.

In the following, the cutting geometries according to the invention are described in greater detail. FIG. 6a is a schematic drawing of a cornea cross-section, illustrating the geometric relationships. The cornea 17 comprises an anterior lamellar layer 100 having an opening cut 110. The posterior lenticule cut consists of a plurality of zones 120, 121, the curvatures of which correspond to the desired refraction correction, and transitions 130 between the zones in the form of steps. In this context, the steps 130 are orientated substantially parallel to the optical axis 140 of the eye.

FIG. 6b is a plan view of the cornea shown in FIG. 6a. In this context, the opening cut 110 is configured in such a way that it leads out of the optical zone of the eye.

FIG. 7a is a schematic drawing of a further cutting geometry in cross-section. In this case, the posterior lenticule cut consists of 3 zones 120, 121 and 122, the curvatures of which correspond to the desired refraction correction, and transitions 130, 131 in the form of steps between the zones. Again, these steps 130, 131 are orientated substantially parallel to the optical axis 140 of the eye. FIG. 7b is a detail illustrating the step 131.

FIG. 8a is a schematic drawing of a further cutting geometry in cross-section. In this case, the posterior lenticule cut likewise consists of 3 zones 120, 121 and 122, the curvatures of which correspond to the desired refraction correction, and transitions 132, 133 between the zones in the form of slopes. FIG. 8b is a detail illustrating the slope 133.

FIG. 9a is a schematic drawing of a further cutting geometry in cross-section. In this context, the posterior lenticule cut likewise consists of 3 zones 120, 121 and 122, the curvatures of which correspond to the desired refraction correction, and rounded transitions 134, 135 between the zones. FIG. 9b is a detail illustrating the rounded transition 135.

FIG. 10 is a schematic drawing of a special cutting geometry for correcting hyperopia in cross-section. In this case, the posterior lenticule cut likewise consists of 3 zones 120, 121 and 122, the curvatures of which correspond to the desired refraction correction, and rounded transitions 136, 137 between the zones. Since the required curvature of the posterior lenticule cut is greater for hyperopia than for myopia, this results in a saw-tooth profile of the posterior lenticule cut.

All of these cutting geometries are distinct in that a lesser volume of material having a lesser maximum thickness than in previous methods has to be removed from the cornea, and the stability of the remaining cornea is thus increased. In many cases of very strong ametropia, a sufficient correction of major sight defects over the entire field of vision is only possible with the above-disclosed solution. It has been shown that the transitions between the zones have an acceptable negative effect on the vision of these patients who would otherwise be visually impaired.

In addition, it should further be noted that the treatment device 1 or the planning device 16 naturally also specifically carries out the method explained generally in the above.

A further embodiment of the planning device is in the form of a computer program or a corresponding data carrier comprising a computer program, which implements the planning device on a corresponding computer, in such a way that the measurement data are inputted to the computer via a suitable data transfer device and the control data are transferred from this computer to the control apparatus 11, for which purpose a data transfer device known to the person skilled in the art may again be used.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A planning device for producing control data for a treatment device for eye surgery which produces at least one cutting surface in a cornea of an eye using a laser device to produce a lenticule for removal from the eye, the planning device comprising:
a calculation module for establishing the at least one cutting surface defining the lenticule, the calculation module being configured to:
establish the at least one cutting surface based on data of a desired refraction correction of the eye,
produce a control data set for actuating the laser device for the at least one cutting surface, and
determine the at least one cutting surface in such a way that it comprises a plurality of zones,
wherein the plurality of zones comprises:
a first correction zone having a first depth and a first curvature, the first curvature being selected to achieve a first refraction correction over the first correction zone, and a second correction zone having a second depth and a second curvature, the second curvature being selected to achieve a second refraction correction over the second correction zone,
wherein the first and second depths differ from each other, and
wherein the first and second refraction corrections are equal to each other and to the desired refraction correction of the eye.

2. The planning device according to claim 1, wherein the calculation module establishes the at least one cutting surface such that a step, a slope, or a rounded transition results between at least the first correction zone and the second correction zone.

3. A treatment device for eye surgery and for producing a lenticule for removal from an eye, comprising:
a laser device, which produces, by laser radiation, at least one cutting surface in a cornea of the eye in accordance with control data, the at least one cutting surface defining the lenticule and the control data corresponding to a desired refraction correction of the eye, and
a planning device for producing the control data, the planning device determining the at least one cutting surface in such a way that the at least one cutting surface comprises a plurality of zones,
wherein the plurality of zones comprises:
a first correction zone having a first depth and a first curvature, the first curvature being selected to achieve a first refraction correction over the first correction zone, and a second correction zone having a second depth and a second curvature, the second curvature being selected to achieve a second refraction correction over the second correction zone,
wherein the first and second depths differ from each other, and
wherein the first and second refraction corrections are equal to each other and to the desired refraction correction of the eye.

4. The treatment device according to claim 3, wherein the planning device establishes the at least one cutting surface such that a step, a slope, or a rounded transition results between at least the first correction zone and the second correction zone.

5. The treatment device recited in claim 3, wherein the laser device is configured to emit focused, pulsed laser radiation into the cornea and produce a cut by adjusting the focus position along the at least one cutting surface.

6. A method for producing control data for a treatment device for eye surgery and for producing a lenticule for removal from an eye, which produces at least one cutting surface in a cornea of the eye using a laser device, the method comprising:
receiving cornea data;
establishing the at least one cutting surface based on a desired refraction correction of the eye, the at least one cutting surface defining the lenticule; and
producing a control data set for the at least one cutting surface for actuating the laser device, the at least one cutting surface being determined so as to comprise a plurality of zones,
wherein the plurality of zones comprises:
a first correction zone having a first depth and a first curvature, the first curvature being selected to achieve a first refraction correction over the first correction zone, and a second correction zone having a second depth and a second curvature, the second curvature being selected to achieve a second refraction correction over the second correction zone,
wherein the first and second depths differ from each other, and
wherein the first and second refraction corrections are equal to each other and to the desired refraction correction of the eye.

7. The method according to claim 6, wherein the at least one cutting surface is determined such that a step, a slope, or a rounded transition results between the first correction zone and the second correction zone.

8. A method for eye surgery including producing at least one cutting surface in a cornea of an eye and producing a lenticule for removal from the eye using a treatment device comprising a laser device, the method comprising:
receiving cornea data;
establishing the at least one cutting surface based on the cornea data and a desired refraction correction of the eye, the at least one cutting surface defining the lenticule;
producing a control data set for the at least one cutting surface;
transmitting the control data set to the treatment device; and
producing the at least one cutting surface by actuating the laser device using the control data set, the at least one cutting surface being determined in such a way that it comprises a plurality of zones,
wherein the plurality of zones comprises:
a first correction zone having a first depth and a first curvature, the first curvature being selected to achieve a first refraction correction over the first correction zone, and a second correction zone having a second depth and a second curvature, the second curvature being selected to achieve a second refraction correction over the second correction zone,
wherein the first and second depths differ from each other, and
wherein the first and second refraction corrections are equal to each other and to the desired refraction correction of the eye.

9. A tangible, non-transient, computer-readable medium having computer-executable instructions stored thereon, the computer-executable instructions including instructions for:
- receiving data about a cornea of an eye;
- establishing at least one cutting surface of the cornea based on a desired refraction correction of the eye, the at least one cutting surface defining a lenticule for removal from the eye; and
- producing a control data set for the at least one cutting surface for actuating a laser device which produces the at least one cutting surface, the at least one cutting surface being determined so as to comprise a plurality of zones,
- wherein the plurality of zones comprises:
  - a first correction zone having a first depth and a first curvature, the first curvature being selected to achieve a first refraction correction over the first correction zone, and a second correction zone having a second depth and a second curvature, the second curvature being selected to achieve a second refraction correction over the second correction zone,
- wherein the first and second depths differ from each other, and
- wherein the first and second refraction corrections are equal to each other and to the desired refraction correction of the eye.

\* \* \* \* \*